US00PP10727P

United States Patent [19]

Olesen et al.

[11] Patent Number: Plant 10,727

[45] Date of Patent: Dec. 22, 1998

[54] MINIATURE ROSE PLANT NAMED 'POULLUTE'

[75] Inventors: L. Pernille Olesen; Mogens N. Olesen, both of Fredensborg, Denmark

[73] Assignee: Poulsen Roser ApS, Fredensborg, Denmark

[21] Appl. No.: 847,109

[22] Filed: May 1, 1997

[51] Int. Cl.[6] ..... A01H 5/00

[52] U.S. Cl. ..... Plt./9

[58] Field of Search ..... Plt./9, 10.1, 7.1

[56] References Cited

PUBLICATIONS

UPOU–ROM, 1997/04, Plant Variety Database, GTI Jouve Retrieval Software, citations for 'POULlute'.

*Primary Examiner*—Howard J. Locker

[57] ABSTRACT

A new pink miniature rose plant which has abundant non-fading flowers and very good keepability. The variety successfully propagates from softwood cuttings and is suitable for year round production in commercial glasshouses. This new and distinct variety has shown to be uniform and stable in the resulting generations from such asexual propagation.

2 Drawing Sheets

SUMMARY OF THE DISCOVERY

The present discovery constitutes a new and distinct variety of miniature rose plant which was discovered in a cultivated area. The mutation resulted from 'POULrouge', a patented variety described and illustrated in U.S. Plant Pat. No. 9,687 and issued on Nov. 12, 1996. The variety is a naturally occurring mutation of unknown causation discovered in a controlled planting as a branch of 'POULrouge'. The new variety is named 'POULlute'.

The rose plant of the present discovery has a unique combination of characeristics which are outstanding in the new variety and which distinguish it from the original rose 'POULrouge' as well as all other varieties which we are aware of. For example, the new variety has:

1. Abundant uniform pink flowers with excellent keepability;

2. Attractive long lasting foliage and compact growth,

3. Year-round flowering under glasshouse conditions;

4. Suitability for production from softwood cuttings in pots;

5. Durable flowers and foliage which make the variety suitable for distribution in the floral industry.

This combination of qualities was lacking in miniature pot rose varieties that were in commercial cultivation and the qualities have been substantially achieved in the new variety.

The resulting mutation was planted in a controlled environment and evaluations were conducted of the resulting rose plants. 'POULlute' was selected by L. Pernille and Mogens N. Olesen in their rose development program in Fredensborg, Denmark in the Spring of 1994.

Asexual reproduction of 'POULlute' by cuttings and traditional budding was first done by L. Pernille and Mogens N. Olesen in August, 1994. This initial and subsequent propagations have demonstrated that the characteristics of 'POULlute' are true to type and are transmitted from one generation to the next.

BRIEF DESCRIPTION OF THE DRAWINGS

The accompanying color illustrations shown as true as is reasonably possible to obtain in color photographs of this type, the typical characteristics of the buds, flowers, leaves, stems, and a plant of 'POULlute'. Specifically illustrated in Sheet 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

Specificaly illustrated in Sheet 2 is a side view of an entire blooming plant in a 12 cm pot.

DETAILED DESCRIPTION OF THE VARIETY

The following is a detailed description of 'POULlute', as observed in its growth in glasshouses in Fredensborg, Denmark and Half Moon Bay, Calif. and in field nursery in Applegate, Oreg. Descriptions were made from plants treated with growth regulators normally used in the greenhouse production process. The growth regulator Paclobutrazol was applied at 30 ppm weekly for three weeks beginning at a plant age of 8 weeks. The penduncle lengths mentioned may actually be shorter and the foliage color several shades darker than on untreated specimens. Color references are made using The Royal Horticultural Society (London, England) Colour Chart, 1995.

For a comparison, the nearest existing rose variety is 'POULrouge', a patented variety described and illustrated in U.S. Plant Pat. No. 9,687 and issued on Nov. 12, 1996. Chart 1 details a physical characteristic of 'POULlute' and the comparison variety.

CHART 1

| Characteristic | 'POULlute' | 'POULrouge' |
|---|---|---|
| Color of middle zone of upper petal | RHS 35 D of the Orange-Red Group | RHS 40 B of the Orange-Red Group |

Mutation resulting from: POULrouge (U.S. Plant Pat. No. 9,687).

Classification:

*Botanical.*—*Rosa hybrida.*

*Commercial.*—Miniature.

Flower and Flower Bud

Blooming cycle: Recurrent.

Flower bud:

*Size.*—14–16 mm in length when petals are just beginning to crack open.

*Bud form.*—Ovoid, short.

*Bud color.*—R.H.S. 35 D Orange-Red Group as petals begin to unfurl.

*Sepals.*—R.H.S. 138 A–138 B of the Green Group. Weak foliaceous appendages and stiff hairs on the margins of three of the five sepals. Surfaces of sepals moderately pubescent.

*Peduncle.*—Surface: Covered uniformly with stiff hairs/light prickles. Length: 25–35 mm average length. Color: Medium green. Prickles: Moderate. Strength: Stiff. Upright.

*Receptacle.*—Surface: Smooth, glabrous. Shape: Urn shaped. Size: Small. 5 mm×5 mm. Color: R.H.S. 138 A of the Green Group.

*Borne.*—2–4 buds per stem.

Flower bloom:

*Diameter.*—Small. 40–50 mm. on average.

*Form.*—Upon opening, pointed ovoid. Completely open, form is convex.

*Petalage.*—Double. Thick, leathery substance. Average range: 30–35.

*Color.*—The middle zone of the petal is colored Orange-Red Group 35D. The petal margin is colored Red Group 36C. The general tonality of the bloom is Red Group 36A. Color only fades slightly towards end of flower life. A spot colored R.H.S. 4 A of the Yellow Group Exists on the inner side of the base of the petal. A spot colored R.H.S. 4 C of the Yellow Group exists on the outer side of the base of the petal.

*Reflex.*—Exterior petals are double reflexed, forming a point. Interior petals are somewhat reflexed.

*Fragrance.*—Light to moderate.

*Duration.*—10–12 days as a cut flower and 13–15 days on the plant.

Reproductive organs:

*Pollen.*—Yellow Group 13B.

*Anthers.*—Size: Small. Color: Yellow Group 13B. Quantity: Numerous.

*Filaments.*—Color: Green-Yellow Group 1B.

*Stigmas.*—Location is superior to anthers.

*Styles.*—Color: Yellow Group 4D.

Plant

Plant growth: Vigorous, compact, upright, bushy. When grown as a 12 cm pot plant, the average height of the plant itself is 20–25 cm and the average width is 20 cm. When grown as a nursery plant on its own roots the average plant height is 35–40 cm and the average plant width is 35–45 cm.

Stems:

*Color.*—Young wood: Green Group 143B. Older wood: R.H.S. 141 B of the Green Group.

*Thorns.*—Form: Straight to slightly concave. Incidence: Average number on main stems and lateral stems. Size: Average length: 3–4 mm. Color: Red Group 39B.

*Bark.*—Young wood: Smooth. Older wood: Smooth.

Plant foliage:

*Normal number of leaflets on average leaves.*—5 leaflets.

*Leaf size.*—Small. 70×50 mm.

*Abundance.*—Average.

*Color, mature foliage.*—Upper leaf surface: Dark green. R.H.S. 137 A of the Green Color Group. Lower leaf surface: Medium green. R.H.S. 136 C of the Green Color Group.

*Color juvenile foliage.*—The upper leaf surface, leaflet margin, and stipule of juvenile foliage is Green Group 143B. The lower leaf surface is between Green Group 139C and 139D. Leaf petiole and leaf rachis of juvenile foliage have limited red intonation of Greyed-Red Group 179B.

Plant leaves and leaflets:

*Stipules.*—Short with stiff hairs. Green Group 138A.

*Petiole.*—Length: 10–12 mm. Underneath: Smooth with occasional prickles.

*Color.*—Green Group 138A.

*Edge.*—Serrated.

*Shape.*—Leaflets are pointed oval.

*Leaflets.*—Number: 5 or 7 on normal leaves.

*Other.*—Moderately glossy finish. Thick texture.

Disease resistance: Variety has average resistance to mildew, rust, black spot, and Botrytris under glasshouse conditions.

We claim:

1. A new and distinct variety of rose plant of the miniature class, substantially as herein illustrated and described, as a distinct and novel rose variety due to its abundant pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

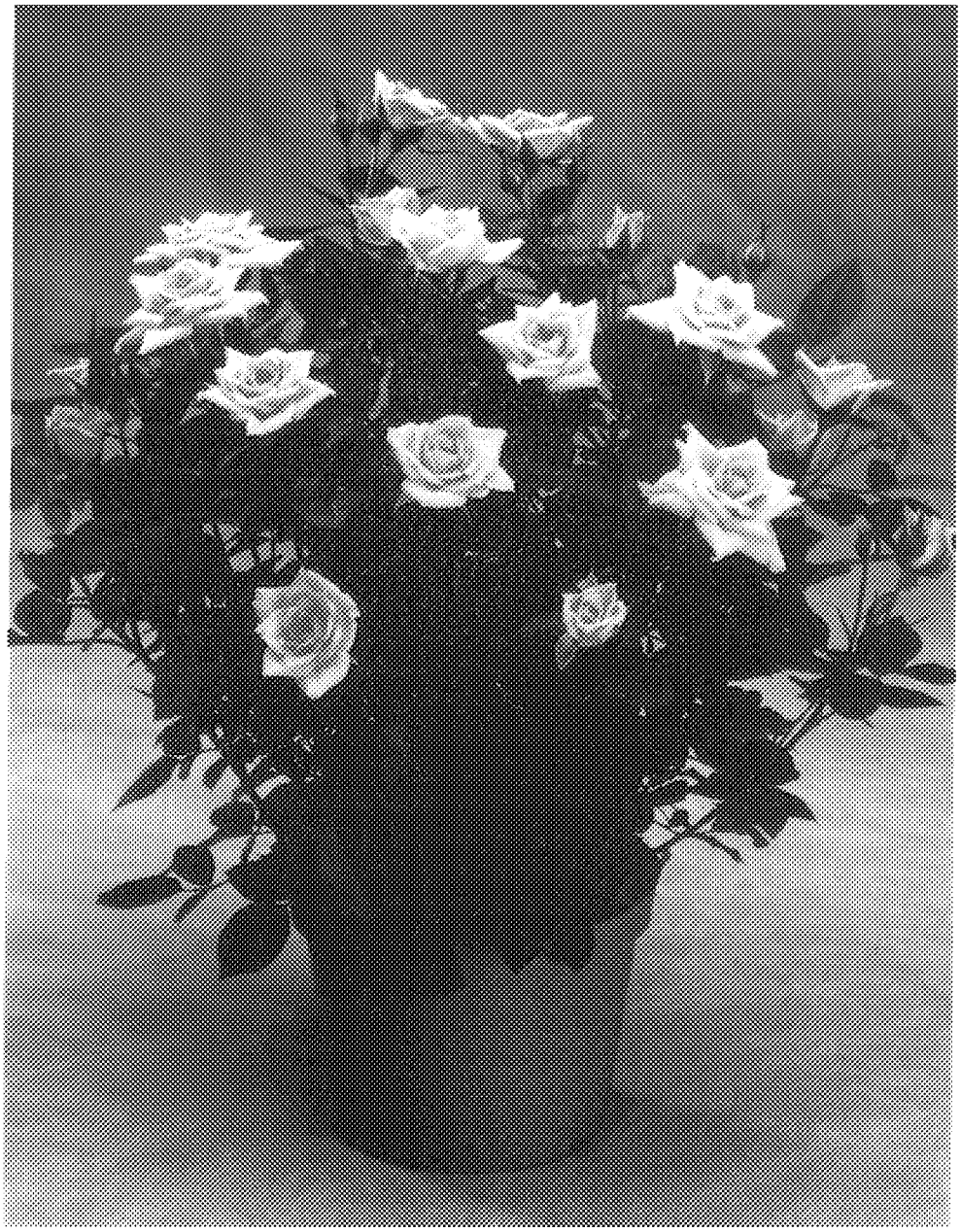

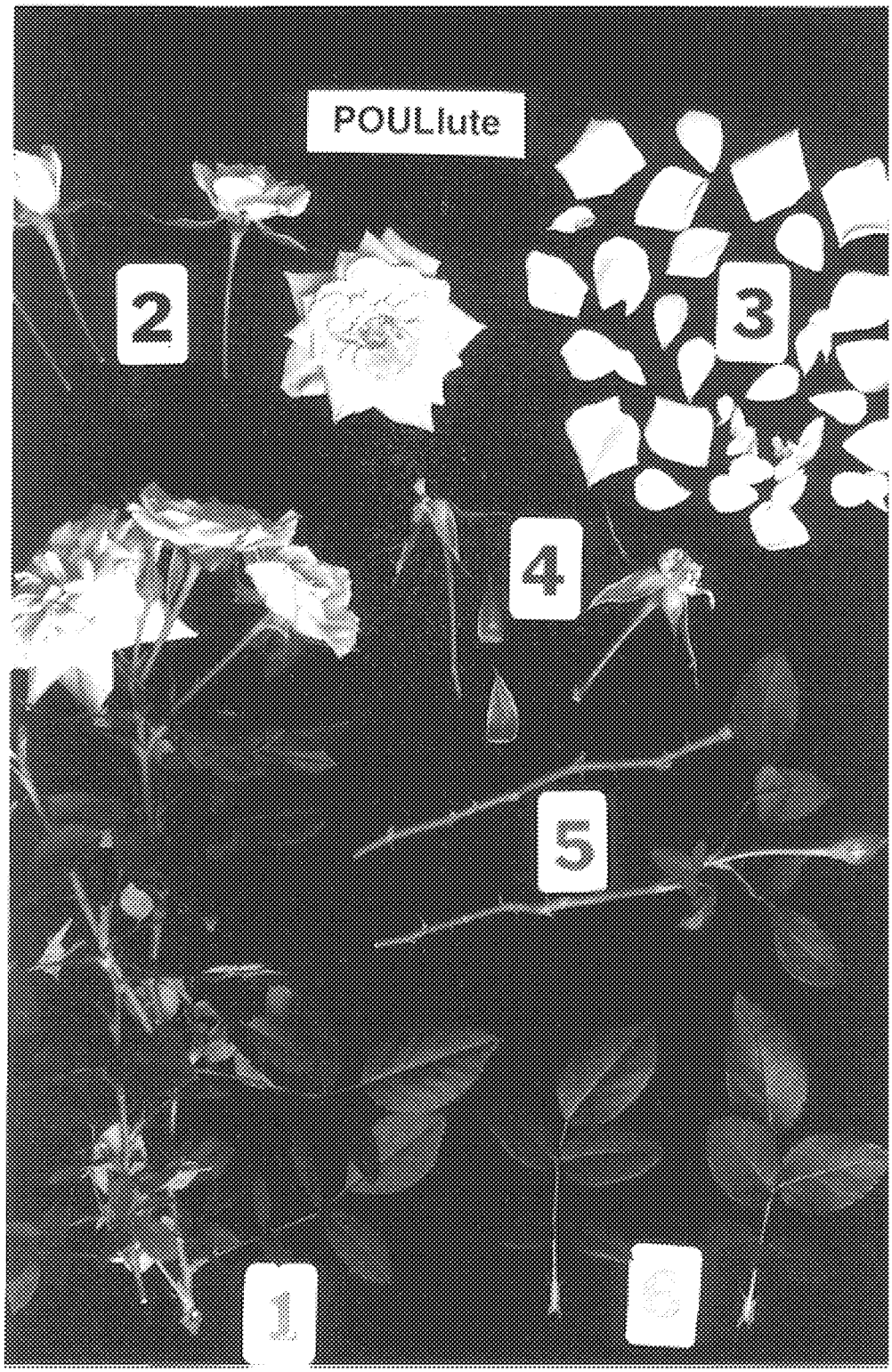
POULlute
2
3
4
5
1
6